United States Patent [19]

Kondo et al.

[11] Patent Number: 4,678,436

[45] Date of Patent: Jul. 7, 1987

[54] COLOR-CHANGEABLE CEMENT COMPOSITION FOR DENTAL USE

[75] Inventors: Kenji Kondo; Shigeru Katsuyama, both of Tokyo; Shoji Akahane, Higashikurume; Kentaro Tomioka, Chofu, all of Japan

[73] Assignee: G-C Dental Industrial Corp., Tokyo, Japan

[21] Appl. No.: 857,162

[22] Filed: Apr. 29, 1986

[30] Foreign Application Priority Data

May 27, 1985 [JP] Japan .................................. 60-113581

[51] Int. Cl.⁴ ................................................ A61K 5/01
[52] U.S. Cl. .................................... 433/228.1; 106/35
[58] Field of Search ........................ 106/35; 433/228.1

[56] References Cited

U.S. PATENT DOCUMENTS 4,526,544 7/1985 Kahn ................................. 523/117

Primary Examiner—Amelia B. Yarbrough
Attorney, Agent, or Firm—Oblon, Fisher, Spivak, McClelland & Maier

[57] ABSTRACT

A color-changeable cement composition for dental use is disclosed, which comprises a first component comprising a metal oxide as a major ingredient, and a second component which can react with the first component to form a set body, wherein the composition contains a substance which changes its color tone with the change in pH so that the color tone of the cement composition can change upon intital setting of the cement composition. The composition enables one to visually observe the degree of setting of the cement composition.

7 Claims, No Drawings

COLOR-CHANGEABLE CEMENT COMPOSITION FOR DENTAL USE

BACKGROUND OF THE INVENTION

This invention relates to a color-changeable cement composition for dental use. Particularly, this invention relates to a color-changeable cement composition which can change the color thereof upon setting of the cement and which enables one to easily judge the state or degree of setting by visual observation.

Now, cement for dental use or dental cement is one of the most prevailing materials that are used clinically by dentists for various applications. For example, it is used for luting of prostheses or orthodontic bands. It is also used for filling the cavity formed by dental caries or for building up, lining, indirect capping, matrix or pit and fissure sealing.

Dental cements widely used at present include zinc phosphate cement, polycarboxylate cement, glass ionomer cement, zinc oxide-eugenol cement, etc. Usually, these cements are used as a mixture of two components, e.g., a mixture of powder and liquid, mixed with each other. The cements are prepared so that they can undergo initial setting within a few minutes after the start of mixing. Therefore, when these cements are used, it is necessary to complete processing or operation while there is an ample allowance in operation, that is, while the mixed cement still has a flowability.

However, it is practically difficult to judge only by visual observation whether or not the mixed dental cement slurry is still in a state where it could be clinically manipulated. It is also practically difficult to judge the extent of area where a glass ionomer cement is actually applied since the glass ionomer cement has a color of crown, when it is used for lining or pit and fissure sealing, although it is highly aesthetic. This is because the glass ionomer cement is translucent and has a color closely resembling that of teeth, which causes the difficulty of discriminating or judging the cement from the tooth substance, resulting in that it is difficult to judge if the cement is applied all over the area intended to be applied, and it is often the case that application is performed on area wider than necessary. Further, when the cement is used for luting of prostheses such as crown, inlay and bridge, it is necessary to eliminate excess cement slurry which is crowded out. In this case, the glass ionomer cement is also difficult to find out where it is crowded out.

SUMMARY OF THE INVENTION

An object of this invention is to provide a dental cement composition obviating the above-described disadvantages of the conventional dental cement compositions.

Another object of this invention is to provide a dental cement composition which enables one to readily judge the timing when the initial setting occurs by visual observation.

Still another object of this invention is to provide a dental cement composition comprising a glass ionomer cement which has a color of crown and is highly aesthetic after setting, and which enables one to easily judge the degree of setting by visual observation.

As a result of extensive investigations by the present inventors, it has been found unexpectedly that a dental cement composition containing a substance which changes its color with the change in pH or a color-changeable substance enables one to easily judge by visual observation the occurrence or the timing of setting without deteriorating physical properties of the cement. Particularly, in the case of a dental glass ionomer cement, addition of a color-changeable substance thereto gives rise to no appreciable influence on the color of the cement after setting and therefore aesthetic property of the desired article is not deteriorated.

The present invention is based on the above-described discovery, and provides a color-changeable cement composition for dental use comprising a first component comprising a metal oxide as a major ingredient, and a second component which can react with the first component to form a set body, wherein said composition contains a substance which changes its color tone with the change in pH so that the color tone of said composition can change upon initial setting of said cement composition.

DETAILED DESCRIPTION OF THE INVENTION

Generally, the basic composition of a dental cement comprises a first component comprising a metal oxide as a major ingredient, and a second component which can react with the first component to form a set body.

Usually, the first component is in the form of powder or paste, while the second component is in the form of liquid, paste or powder, and these components are used in combination. When both the components are in the form of powder, they are premixed before use so that it is sufficient to add only water upon mixing.

When the components are in the form other than a mixture of powder and powder, they are mixed upon mixing. If it is desired, a portion of the second component may be included in the first component beforehand. As stated above, various forms of dental cement compositions can be used in this invention. Various combinations of the components, for example, powder-liquid, powder-paste, paste-paste, paste-liquid, liquid-liquid can be used. In addition, it is also possible to use a combination of powder of the first component, powder of the second component and water.

The color-changeable substance, i.e., substance which can change its color tone with the change in pH, can be added either to the first component or to the second component of the dental cement composition which may be of various forms.

The metal oxide, which is the major ingredient of the first component, may be a sinter of two or more oxides which is prepared by sintering a simple metal oxide such as zinc oxide and calcium oxide or a mixture of zinc oxide as a major ingredient and one or more other oxides or fluorides, and pulverizing the resulting sintered body. The metal oxide may be a vitreous oxide prepared by melting the oxide to a glass state. The vitreous oxide includes fluoroaluminosilicate glass which is used in dental glass ionomer cements.

The second component which can react with the first component to form a set body is not limited particularly. Suitable examples of the second component include acidic substances such as phosphoric acid, polycarboxylic acids, etc. and chelating agents such as eugenol, etc.

With respect to the proportion of the color-changeable substance, it is sufficient to use the substance in an amount of 1.0% by weight or less based on the total weight of the dental cement composition. Usually, it is used in an amount of 0.0001 to 0.5% by weight, preferably 0.0001 to 0.05% by weight. When the amount of the color-changeable substance is less than 0.0001% by weight, no appreciable influence is given on the color tone of the cement. On the other hand, when it is above 0.5% by weight, coloring occurs to an extent more than that is intended. Particularly, in the case of a glass ionomer cement, aesthetic property is deteriorated.

The color-changeable substance can be added to the first component and/or the second component.

The color-changeable substances which can be used in this invention are selected from a wide range of substances by measuring the pH change of mixed cement slurry or paste, and choosing appropriate substances which change their color at a desired pH value within the range of pH to be used. For example, pH indicators can be used as such color-changeable substance.

Generally, the pH of a mixed dental cement slurry changes from acidic to neutral according to its setting process. It is therefore preferred that the color-changeable substances have a discoloring characteristic at a pH of 7 or less.

Suitable examples of pH indicators which can be used in this invention include methyl violet, crystal violet, ethyl violet, malachite green oxalate, methyl green, 2-(p-dimethyl-aminophenylazo)pyridine, cresol red, quinaldine red, para methyl red, metanil yellow, 4-phenylazodiphenylamine, thymol blue, m-cresol purple, orange IV, 4-o-tolylazo-o-toluidine, erythrosine disodium salt, benzopurpurine 4B, N,N-dimethyl-p-(m-tolylazo)-aniline, 2,4-dinitrophenol, N,N-dimethyl-p-phenylazoaniline, 4,4'-bis(2-amino-1-naphthylazo)-2,2'-stilbenedisulfonic acid, tetrabromophenolphthalein ethyl ester potassium salt, bromophenol, Congo red, methyl orange-xylene cyanole solution, methyl orange, ethyl orange, 4-(4-dimethylamino-1-naphthylazo)-3-methoxybenzenesulfonic acid, bromocresol green, resazurin, 4-phenylazo-1-naphthylamine, ethyl red, 2-(p-dimethylamino-1-naphthylazo)pyridine, 4-(p-ethoxyphenylazo)-m-phenylendiamine monohydrochloride, lacmoid, alizarin red S, methyl red, propyl red, cromocresol purple, chlorophenol red, p-nitrophenol, alizarin, 2-(2,4-dinitrophenylazo)-1-naphthol-3,6-disulfonic acid disodium salt, etc.

Such pH indicators can be mixed with the cement composition by conventional mixing methods. For example, they can be mixed with a powder component in a mortar until a uniform mixture can be obtained. Alternatively, a method can be used in which the pH indicators are dissolved in a solvent such as ethyl alcohol or water, and the surface of a metal oxide is treated with the resulting solution followed by removal of the solvent. Those pH indicators which are soluble in liquid can be previously dissolved in the liquid.

The dental cement composition of this invention can be prepared by adding a substance which can change its color with the change in pH to a cement composition comprising the first and second components, e.g., zinc phosphate cement, silicate cement, zinc oxide-eugenol cement, glass ionomer cement, and polycarboxylate cement.

This invention will be described in greater detail with reference to the following examples and comparative examples. However, this invention is not construed as being limited to these examples.

EXAMPLE 1

One hundred (100) grams of powder of GC Livcenera (trade name for a product of G-C Dental Industrial Co., Ltd.) and 0.03 g of Meta Cresol Purple were mixed well in a mortar. The resulting mixed powder (2.0 g) and 1.0 g of a liquid of GC Livcenera were mixed, and the discoloration of the cement slurry was observed visually. As the result, it was confirmed that the color tone of the cement changed from red to yellow. The period of time required for this change coincided with that of initial setting. Therefore, the extent or degree of setting was easily judged by visual observation.

EXAMPLE 2

One hundred (100) grams of powder of GC Fuji Ionomer Type I (trade name for a product of G-C Dental Industrial Co., Ltd.) and 20 g of a 0.01% methanol solution of cresol red were mixed well in a mortar, and then methanol was removed by evaporation. The resulting mixed powder (1.4 g) and 1.0 g of liquid of GC Fuji Ionomer Type I were mixed, and the discoloration of the cement slurry was observed visually. As the result, it was confirmed that the color tone of the cement changed from red to yellow. The period of time required for this change coincided with that of setting. Thus, the degree of setting was easily judged by visual observation.

EXAMPLE 3

One hundred (100) grams of powder of GC Lining Cement (trade name for a product of G-C Dental Industrial Co., Ltd.) and 20 g of a 0.02% ethanol solution of thymol blue were mixed well in a mortar, and then ethanol was removed by evaporation. The resulting mixed powder (1.2 g) and 1.0 g of GC Lining Cement Liquid were mixed. The resulging mixture was applied for lining on an extracted tooth having formed therein a cavity due to dental caries, and the discoloration of the cement slurry was visually observed. As the result, it was confirmed that the color of the cement slurry changed from red to yellow. The period of time required for this color change coincided with that of setting, and the degree of setting could be easily judged by visual observation. Further, it was possible to judge the presence of the cement without difficulty since the cement composition showed a color tone different from that of tooth substance until it set so that failure or excessive application was avoided.

EXAMPLE 4

One hundred (100) grams of powder of GC Elite Cement 100 (trade name for a product of G-C Dental Industrial Co., Ltd.) and 20 g of a 0.05% ethanol solution of m-cresol purple were mixed well in a mortar, and then ethanol was removed by evaporation. The resulting powder (1.45 g) and 0.5 ml of GC Elite Cement 100 liquid were mixed. The resulting mixture was subjected to observation of possible discoloration. As the result, it was confirmed that the color of the cement slurry changed from red to yellow. The period of time required for this color change coincided with that of setting. Thus, the degree of setting could be judged easily by visual observation.

EXAMPLE 5

One hundred (100) grams of liquid of GC Eugenol Cement (trade name for a product of G-C Dental Industrial Co., Ltd.) and 0.004 g of ethyl orange were mixed and stirred until the latter was dissolved. The resulting liquid (0.35 g) and powder of GC Eugenol Cement (1.0 g) were mixed. The discoloration of the cement slurry was visually observed. As the result, it was confirmed that the color of the cement changed from red to yellow. The period of time required for this change coincided with that of setting, and the degree of setting was easily judged by visual observation.

COMPARATIVE EXAMPLE 1

Powder of GC Livcenera (trade name for a product of G-C Dental Industrial Co., Ltd.) 2.0 g and 1.0 g of liquid of GC Livcenera liquid were mixed and the state of setting was observed in the same manner as in Example 1. As the result, the degree of setting was not easily judged by visual observation since the resulting cement slurry did not change its color.

COMPARATIVE EXAMPLE 2

Powder of GC Fuji Ionomer Type I (trade name for a product of G-C Dental Industrial Co., Ltd.) 1.4 g and 1.0 g of liquid of GC Fuji Ionomer Type I were mixed, and the state of setting was observed in the same manner as in Example 2. As the result, the degree of setting could not easily judged by visual observation since the resulting cement slurry did not change its color.

COMPARATIVE EXAMPLE 3

Powder of GC Lining Cement (trade name for a product of G-C Dental Industrial Co., Ltd.) 1.2 g and 1.0 g of liquid of GC Lining Cement were mixed and the state of setting was observed in the same manner as in Example 3. As the result, the degree of setting could not easily be judged by visual observation since the resulting cement slurry did not change its color. In addition, since the color tone of the cement slurry before setting closely resembled that of tooth substance, it was difficult to judge the presence of the cement.

COMPARATIVE EXAMPLE 4

Powder of GC Elite Cement 100 1.45 g and 0.5 ml of liquid of GC Elite Cement 100 were mixed, and the state of setting was observed in the same manner as in Example 4. As the result, the degree of setting could not be easily judged by visual observation since the resulting cement slurry did not change its color.

COMPARATIVE EXAMPLE 5

Powder of GC Eugenol Cement (trade name for a product of G-C Dental Industrial Co., Ltd.) 1.0 g and 0.35 g of liquid of GC Eugenol Cement were mixed, and the state of setting was observed in the same manner as in Example 5. As the result, the degree of setting could not be easily judged by visual observation since the resulting cement slurry did not change its color.

From the results in the foregoing, it can be seen that the color-changeable dental cement composition of Examples 1 to 5 are superior over the dental cement compositions of Comparative Examples 1 to 5.

Although the invention has been described with preferred embodiments, it is to be understood that variations and modifications may be employed as will be apparent to those skilled in the art. Such variations and modifications are to be considered within the purview and scope of the claims appended hereto.

What is claimed is:

1. A color-changeable cement composition for dental use comprising a first component comprising a metal oxide as a major ingredient, and a second component which reacts with the first component to form a set body, wherein said composition contains a substance which changes its color tone with the change in pH so that the color tone of said composition changes upon initial setting of said cement composition.

2. The color-changeable cement composition as claimed in claim 1, wherein said dental cement composition contains a dental cement selected from the group consisting of dental zinc phosphate cement, dental polycarboxylate cement, dental glass ionomer cement, dental zinc oxide-eugenol cement.

3. The color-changeable cement composition as claimed in claim 1, wherein said substance which changes its color tone with the change in pH is present in an amount of 0.0001 to 0.5% by weight based on the total weight of said color-changeable cement composition.

4. The color-changeable cement composition as claimed in claim 2, wherein said substance which changes its color tone with the change in pH is present in an amount of 0.0001 to 0.5% by weight based on the total weight of said color-changeable cement composition.

5. The color-changeable cement composition as claimed in claim 1, wherein said substance which changes its color tone with the change in pH is a pH indicator.

6. The color-changeable cement composition as claimed in claim 5, wherein said pH indicator has a discoloring characteristic at a pH of 7 or less.

7. The color-changeable cement composition as claimed in claim 5, wherein said pH indicator is selected from the group consisting of meta-cresol purple, cresol red; thymol blue and ethyl orange.

* * * * *